United States Patent [19]

Chang et al.

[11] Patent Number: 4,638,095
[45] Date of Patent: Jan. 20, 1987

[54] ISOLATION OF A NOVEL ANTIOXIDANT ROSMARIDIPHENOL FROM *ROSMARINUS OFFICINALIS* L.

[75] Inventors: Stephen S. Chang; Chi-Tang Ho, both of East Brunswick; Christopher M. Houlihan, Parsippany, all of N.J.

[73] Assignee: Research Corporation, New York, N.Y.

[21] Appl. No.: 639,899

[22] Filed: Aug. 10, 1984

[51] Int. Cl.⁴ ............................................ C07C 49/573
[52] U.S. Cl. .................................................... 568/326
[58] Field of Search ........................................ 568/326

[56] References Cited

U.S. PATENT DOCUMENTS

| | | | |
|---|---|---|---|
| 3,497,532 | 2/1970 | Woodward | 568/326 |
| 3,950,266 | 4/1976 | Chang et al. | 252/398 |
| 4,051,260 | 9/1977 | Nelson et al. | 568/326 |

FOREIGN PATENT DOCUMENTS

| | | | |
|---|---|---|---|
| 58-208383 | 12/1983 | Japan | 568/326 |
| 58-225199 | 12/1983 | Japan | 568/326 |
| 2033768 | 5/1980 | United Kingdom | 568/326 |

OTHER PUBLICATIONS

Chang et al., J. Food Sci., vol. 42, pp. 1102–1106 (1977).
Wu et al., J.A.OCS, vol. 59, pp. 339–345 (1982).
Inatani et al., Agric. Biol. Chem., vol. 46, pp. 1601–1666 (1982), vol. 47, pp. 521–528 (1983).
Nakatani et al., Agric. Biol. Chem., vol. 48, pp. 2081–2085 (1984).
Fenaroli, "Handbook of Flavor Ingredients", vol. 1, p. 453 (1984).
Dostert et al., Chem. Abst., vol. 73, #45210s(1970).
Nathan et al., Chem. Abst., vol. 65, #13629b-c (1965).
Blomkviest, G. B.; Jansson, K. M., Ryhage, E. R.; Osterdahl, B. G., *J. Agric. Food Chem.* 1986, 34, 274–276.
Surman, D. J., Vickerman, J. C., *J. Chem. Soc., Chem. Commun.* 1981, 324–325.
Barber, M.; Bordoli, R. S.; Sedgwick, R. D.; Tyler, A. N., *J. Chem. Soc., Chem. Commun. 1981*, 325–327.

*Primary Examiner*—James H. Reamer
*Attorney, Agent, or Firm*—Scully, Scott, Murphy & Presser

[57] ABSTRACT

This disclosure describes the extraction of a novel antioxidant, Rosmaridiphenol, isolated from the leaves of Rosemary.

1 Claim, 5 Drawing Figures

Structure of Rosmaridiphenol

Proton NMR Spectrum of Rosmaridiphenol

C-13 NMR Spectra of Rosmaridiphenol; Upper: off-resonance decoupled
Bottom: Noise-decoupled Expanded off-resonance decoupled C-13 NMR Spectrum of Rosmaridiphenol J-Modulation Study in C-13 NMR Spectrum of Rosmaridiphenol

ISOLATION OF A NOVEL ANTIOXIDANT ROSMARIDIPHENOL FROM *ROSMARINUS OFFICINALIS* L.

BACKGROUND OF THE INVENTION

The invention relates to a novel antioxidant. As is well known, fats and oils become rancid or otherwise unpleasant as to flavor or odor by reason of oxidation effects. A number of chemical compounds have been employed for avoiding or reducing these effects, i.e. so that the fats and oils, or foods containing them, may be kept for longer periods of time, but such agents have not been entirely satisfactory or effective in many cases. Furthermore, they are chemical products not derived from or identical with material of natural food classifications, and there has been some question about the advisability of using them.

The most commonly used antioxidants at the present time are BHA (butylated hydroxyanisole) and BHT (butylated hydroxytoluene). They are added to a wide variety of foods on the market. However, they are quite volatile and easily decomposed at high temperatures. Consequently, they are not satisfactory for such common food products as French fries, potato chips, etc. Furthermore, they are not effective in vegetable oils and in preventing the development of initial off-flavors, such as the reversion flavor. The newly developed TBHQ (tertiary butylhydroquinone) has an excellent ability to retard the absorption of oxygen. However, it does not seem to retard the development of objectionable flavors. Fried noodles stabilized with TBHQ are known to absorb less oxygen than those stabilized with BHT. However, the fried noodles stabilized with TBHQ developed a strong rancidity odor before that observed in the sample stabilized with BHT. It is also known that soybean oil stabilized with TBHQ has a lower peroxide number during storage, but develops a stronger objectionable flavor.

In any event, the commonly used antioxidants today are synthetic chemicals. There is a tendency for the consumers to reject them.

Furthermore, the possible toxicity of the synthetic chemicals used as antioxidants have been a subject of study for many years (Johnson and Hewgill, 1961; Branen, 1975). In an issue of the "Food Chemical News" (1976), the concern of the FDA on the use of BHT was reported. The concern stems from scientific literature reviews conducted for the FDA which focused on the enzyme-inducing effects of BHT on liver and on extraheptic organs, such as the lungs and gastrointestinal tract mucosa. The article also reported that the FDA has expressed an interest in the effect of BHT on the conversion of other ingested materials into toxic substances or carcinogens by the increase of microsomal enzymes. This is certainly nothing new because restrictions have been placed upon the use of such synthetic antioxidants by many European and Asiatic countries.

All this leads to the interest of preparing antioxidants from natural food stuffs by extraction, purification and fractionation. Certainly, there is no assurance whatsoever that a fraction or a compound isolated from natural food is safe. Nevertheless, such an antioxidant would be natural identicals, not a synthetic chemical, but rather a natural component of foods which we have been eating for thousands of years.

It has heretofore been found that antioxidant properties are possessed by certain natural vegetable materials in the class sometimes identified as herbs, and particularly in the specific plants rosemary and sage, which are commonly used as spices. Indeed it has been found that by extracting the fresh or dried leaves or like parts of these plants, such as rosemary, by the use of alcohol or similar readily volatile solvent a somewhat concentrated but crude preparation may be obtained which has considerable antioxidant effect. Procedures have been proposed for making such crude extract, in most instances directly from the leaves, stems or the like of the natural spice, or in some cases by alcohol treatment of the plant material after the oil of the spice (present in very minor proportion) has been substantially removed by steam distillation. The resulting crude extract in alcohol or like liquid has been evaporated (sometimes after some bleaching with active carbon) to yield a solid product. While such product can be considered as in some respect refined in contrast with the original leaves and stems of the spice plant, and indeed although such products have been described as purified and of substantially less taste or odor than the natural spice, these materials have not be any means been fully freed of the characteristically pungent, natural aroma and flavor, with some bitterness, of the basic spice material. Accordingly, although such preparations have been found to provide antioxidant properties, and one such product is currently available on the market, the use of these materials is limited to situations where the basic flavor of the spice is wanted or at least tolerated.

So far as can be ascertained, essentially tasteless and odorless antioxidant materials are limited to substances such as those of the manufactured chemical character mentioned above, and indeed it can be said that there is a real need in the food industry for an antioxidant extracted from natural food stuffs, that has superior properties and can serve a wide range of uses.

BRIEF SUMMARY OF THE INVENTION

The present invention relates to a novel antioxidant isolated from the leaves of *Rosmarinus officinalis* L. The novel antioxidant has been named Rosmaridiphenol.

DETAILED DESCRIPTION OF THE INVENTION

The new diphenolic diterpene has the structure.

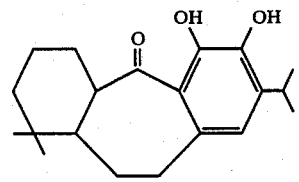

The above structure is based on Infrared (IR) Spectrum, Mass Spectrum, Proton Nuclear Magnetic Resonance ($^1$H-NMR) Spectrum, and C-Thirteen Carbon Nuclear Magnetic Resonance ($^{13}$C-NMR) Spectrum some of which are shown in the accompanying figures.

Figure 1:
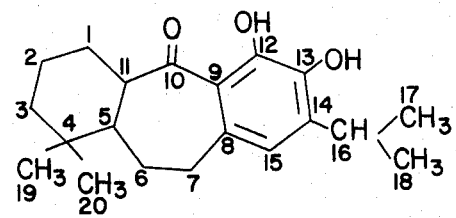

FIG. 1. Structure of Rosmaridiphenol.

Figure 2:
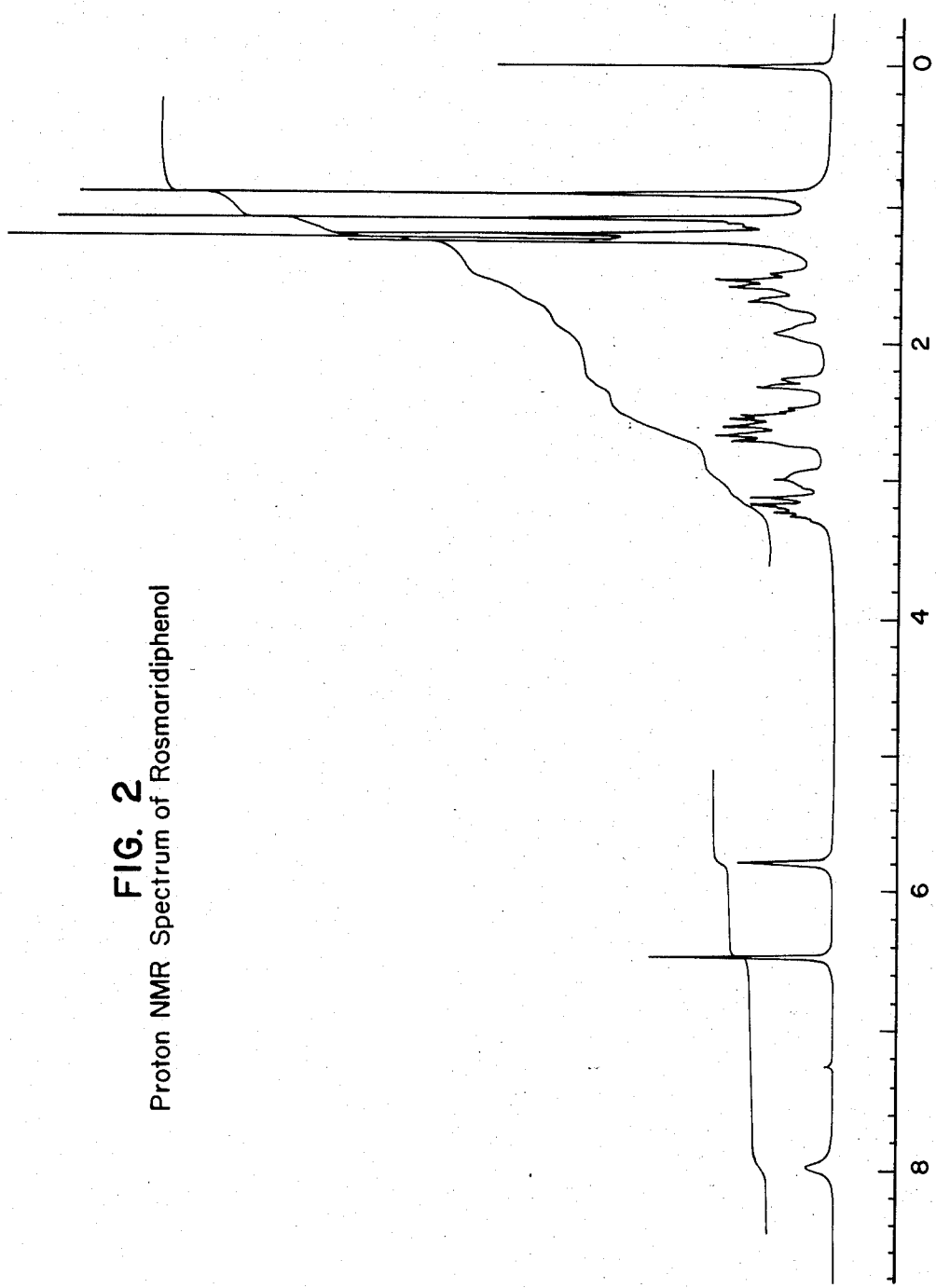

FIG. 2. Proton NMR Spectrum of Rosmaridiphenol.

Figure 3:
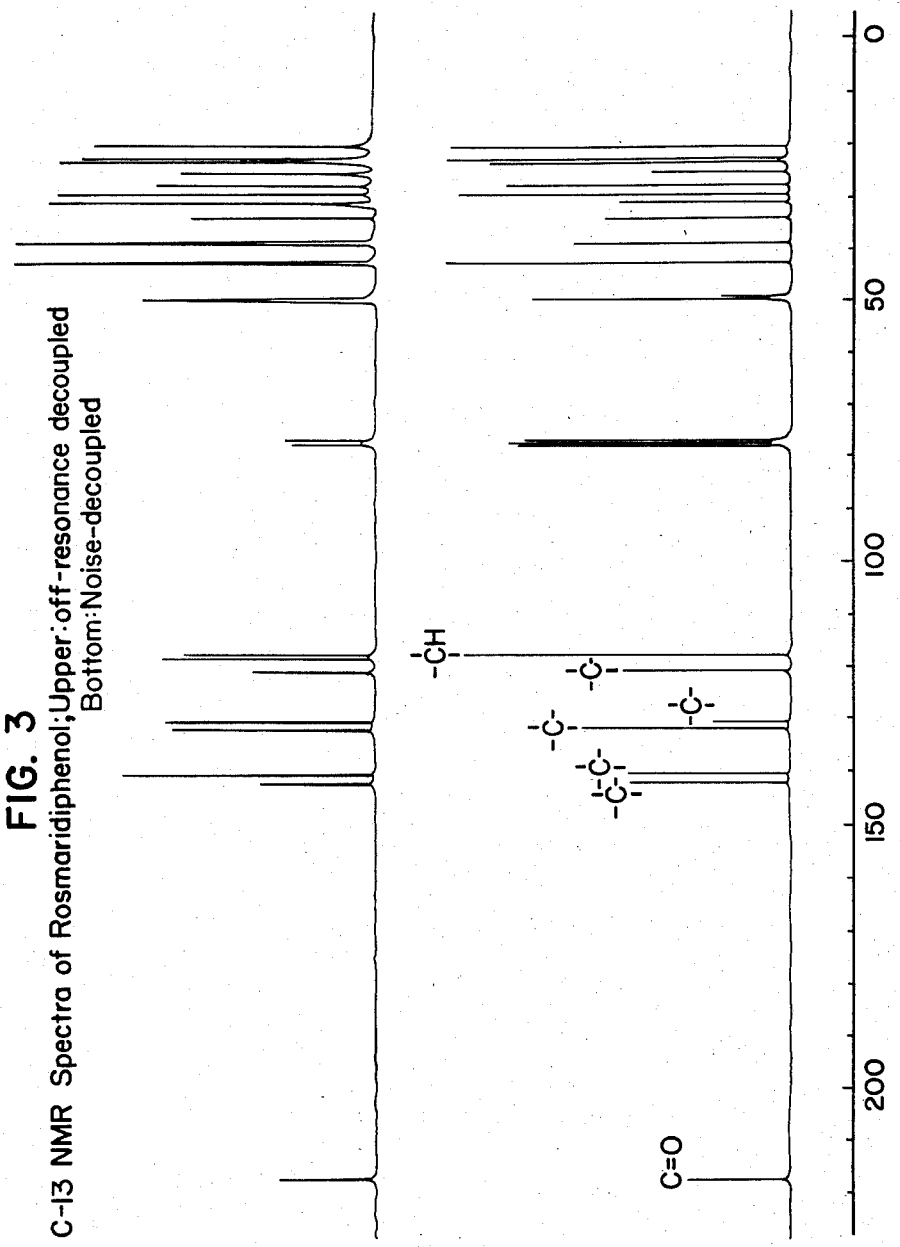

FIG. 3. C-13 NMR Spectrum of Rosmaridiphenol; Upper: off-resonance decoupled; Bottom: Noise decoupled.

Figure 4:
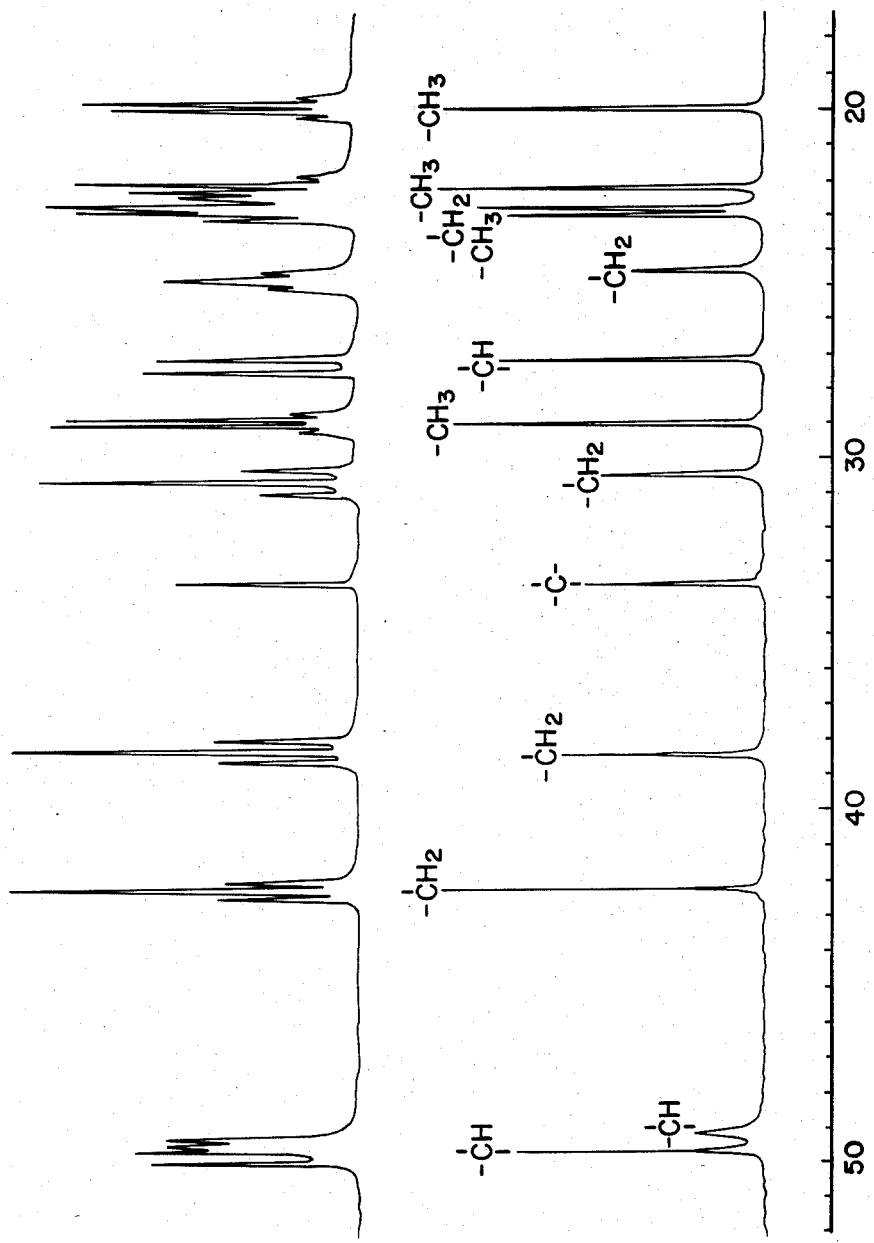

FIG. 4. Expanded off-resonance decoupled C-13 NMR Spectrum of Rosmaridiphenol.

Figure 5:
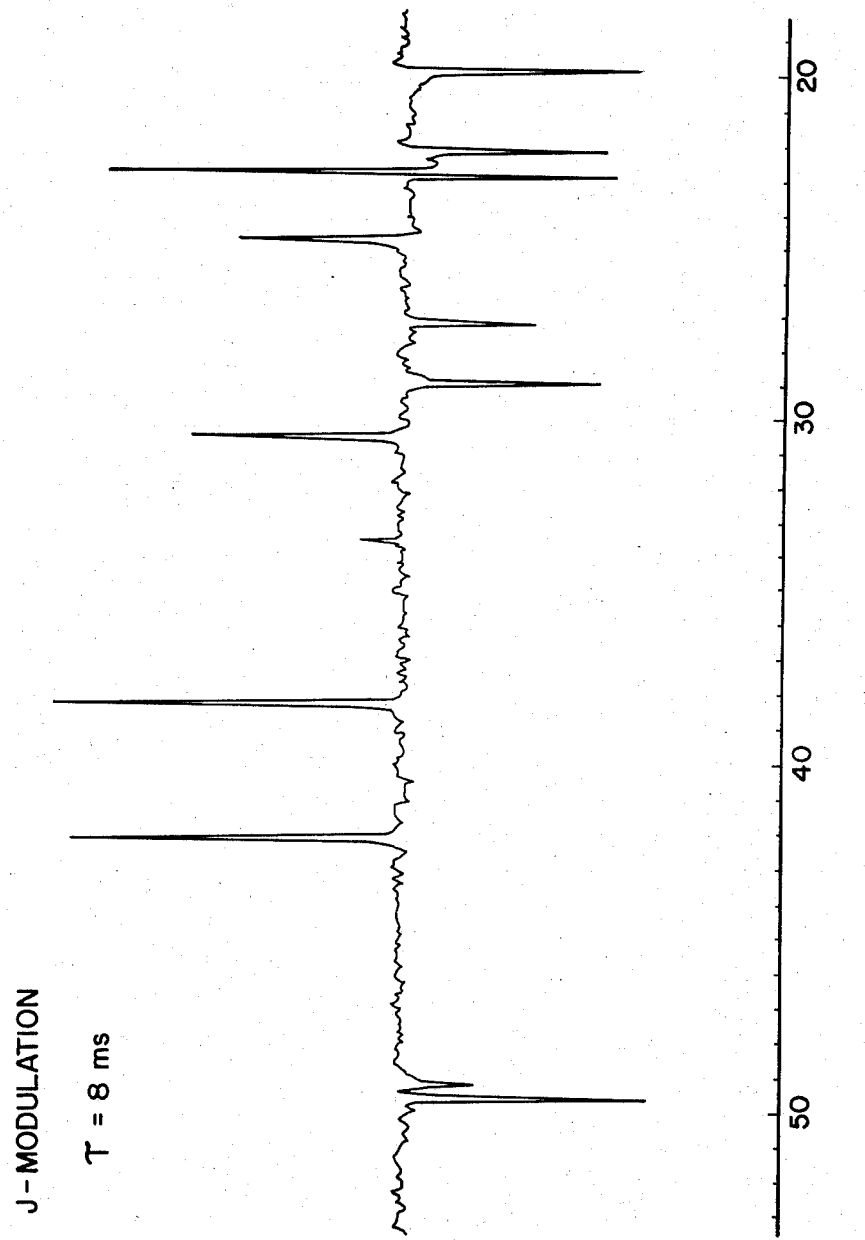

FIG. 5. J-Modulation Study in C-13 NMR Spectrum of Rosmaridiphenol.

The novel antioxidant was extracted from dried, ground Rosemary leaves following a procedure described by Wu, et al. JAOCS 59:339 (1981) which is incorporated herein by reference. Following a vacuum steam distillation process, this extract was fractionated using a 5 cm × 122 cm glass column packed with activated silicic acid. Activation of this adsorbent was accomplished by a procedure set forth by Sahasrabudhe and Chapman (1961). The column was eluted by stepwise gradient using 100% hexane as the initial eluent and then employing the following solutions of diethyl ether in hexane (E/H); 5% E/H, 10% E/H, 15% E/H, 25% E/H, 50% E/H and 75% E/H. The final eluent of this separation was 100% methanol. A total of 15 fractions resulted from this elution pattern.

The infrared spectrum of this antioxidant compound was obtained using a KBr pellet on a Beckman Acculab 4 Infrared Spectrophotometer. A mass spectrum was acquired utilizing a Du Pont 21-490 Mass Spectrometer. The source temperature was held at 200° C. with the ionization voltage at 70 eV. All of the proton and carbon-13 NMR spectra were obtained using a Bruker UM-250 NMR Spectrometer.

Upon chromatographic separation of the vacuum steam distilled Rosemary extract, the 75:25 diethyl ether:hexane fraction was found to be composed of many white crystals dispersed in a thick yellow liquid. Using a cold 75:25 ether:hexane solution, the white crystals were separated from the viscous portion of this fraction and filtered using a Buchner funnel. The crystals were then recrystallized twice using 100% ethanol. After the second recrystallization, these white, fluffy crystals were filtered with cold ethanol and collected.

Through spectroscopic methods, the isolated white crystals were identified and named Rosmaridiphenol (structure shown in FIG. 1), $C_{20}H_{28}O_3$, m.p. 182°–184° C. The elemental analysis of Rosmaridiphenol concluded that this compound was 75.75% carbon and 8.73% hydrogen. These percentages were almost identical to the values calculated from this compound's molecular formula of 75.81% carbon and 8.91% hydrogen.

The IR spectrum of Rosmaridiphenol revealed the presence of hydroxy groups by absorptions at 3520, 3480 and 3250 $cm^{-1}$. Also, there were indications of an aromatic ring corresponding to peaks at 3020 and 1580 $c^{-1}$. In addition, a conjugated keto group band was seen at 1680 $cm^{-1}$. The other IR absorptions of this molecule were at 2950, 2850, 1580, 1500, 1465, 1450, 1380, 1280, 1160, 1100, 1025, 1000, 960, 880, 700 and 650 $cm^{-1}$.

Rosmaridiphenol's mass spectrum showed a very stable molecular ion at m/z (relative intensity) 301 (25%), 283 (7%), 273 (5%), 260 (10%), 247 (10%), 217 (14%) and 179 (12%). The peak at m/z 301 demonstrated the loss of a methyl group from the parent ion. The small peak appearing at m/z 273 suggested the loss of the isopropyl group from this molecule.

The proton NMR spectrum of Rosmaridiphenol appears in FIG. 2. As the $^1H$ NMR spectrum shows, the phenolic protons appeared as singlets at 7.90 and 5.80 ppm. The hydrogen of the phenolic group of carbon No. 12 was shifted downfield due to intramolecular hydrogen bonding with the keto group of this molecule. The only aromatic proton of Rosmaridiphenol was seen characteristically as a singlet at 6.50 ppm.

The gem-dimethyl hydrogen atoms appeared as singlets at 1.1 and 0.9 ppm. The protons of the methyl groups of the isopropyl structure gave confusing spectroscopic results. In the $^1H$ NMR spectrum of this molecule, the absorption at 1.2 ppm appeared to be a triplet. In reality, these two methyl groups exhibited two closely spaced doublets that appeared as a triplet due to overlapping. This conclusion was proven when the methine hydrogen of the isopropyl group (which appeared as a septet at 3.3 ppm) was irradiated and two narrowly spaced singlets resulted from the "triplet" at 1.2 ppm. The other aliphatic protons appeared as multiplets between 1.6 and 3.2 ppm.

The Carbon-13 NMR spectrum of Rosmaridiphenol is shown in FIG. 3. Other Carbon-13 NMR experiments were performed, including an off-resonance type (FIG. 4) and a J-modulation study (FIG. 5). The phenolic carbon atoms appeared characteristically in the $^{13}C$ NMR spectrum at 143 and 141 ppm. The expanded off-resonance spectrum between 110 and 150 ppm indicated a lone aromatic C-H group at 118 ppm, which corresponded to Carbon No. 15. The other aromatic carbon atoms absorbed at 121, 131 and 133 ppm.

From the off-resonance and J-modulation spectra it was determined that there were four methyl carbon atoms. The $CH_3$ groups of the isopropyl structure appeared at 22.3 and 23.0 ppm. The gem-dimethyl carbon atoms, numbered 19 and 20, were assigned abosorptions at 29.2 and 20.1 ppm, respectively. Also the off-resonance spectrum (FIG. 4) showed one methine group and one quaternary carbon atom. From this information it was concluded that Carbon No. 16 appeared at 27.0 and Carbon No. 4 was responsible for the signal at 34.4 ppm. The peaks at 50.2 and 49.3 ppm were assigned to the "fused" carbon atoms numbered 5 and 11. The other five aliphatic carbon atoms resulted in signals that appeared between 23.0 and 42.0 ppm.

The keto group carbon atom appeared at 217 ppm. This absorption was shifted downfield again due to intramolecular hydrogen bonding.

All of the spectroscopic data obtained are in accordance with the proposed structure of Rosmaridiphenol.

Rosmaridiphenol was tested for antioxidative effectiveness at a concentration of 0.02% in prime steam lard. This fat substrate was maintained at 60° C. in the dark for the duration of the experiment. Antioxidant activity was based on the peroxide inhibiting capacity of the compound tested. The peroxide values obtained from Rosmaridiphenol and other standard antioxidants appear in Table I. The antioxidant activity of Rosmaridiphenol surpassed BHA and approached the effectiveness of BHT.

TABLE I

Antioxidant Activity of Rosmaridiphenol and other Commercial Antioxidants

| Additive (0.02%) | Peroxide Value (Meq/Kg) in Prime Steam Lard at 60° C. after days: (Average of Two Samples) | | | |
|---|---|---|---|---|
| | 7 | 14 | 21 | 28 |
| Control—no additive | 4.70 | 10.08 | 29.93 | 119.67 |
| BHT | 1.26 | 1.86 | 2.71 | 3.37 |
| BHA | 2.72 | 6.54 | 12.10 | 17.01 |
| Rosmaridiphenol | 1.57 | 2.30 | 3.10 | 4.09 |

What is claimed is:

1. A compound of the formula:
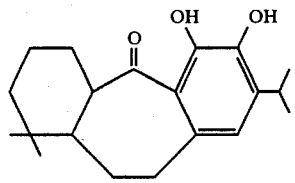
* * * * *